United States Patent
Linder et al.

(10) Patent No.: US 6,884,437 B2
(45) Date of Patent: Apr. 26, 2005

(54) ADMINISTRATION FORM COMPRISING AN ACID-LABILE ACTIVE COMPOUND

(75) Inventors: Rudolf Linder, Constance (DE); Rango Dietrich, Constance (DE)

(73) Assignee: Byk Gulden Lomberg Chemische Fabrik GmbH, Constance (DE)

( * ) Notice: Subject to any disclaimer, the term of this patent is extended or adjusted under 35 U.S.C. 154(b) by 2 days.

(21) Appl. No.: 10/423,002

(22) Filed: Apr. 25, 2003

(65) Prior Publication Data

US 2004/0022854 A1 Feb. 5, 2004

Related U.S. Application Data

(62) Division of application No. 09/983,990, filed on Oct. 26, 2001, now Pat. No. 6,569,453, which is a continuation of application No. 09/530,944, filed as application No. PCT/EP98/08036 on Dec. 8, 1998, now Pat. No. 6,328,993.

(30) Foreign Application Priority Data

Dec. 8, 1997 (DE) .......................... 197 54 324
May 20, 1998 (DE) .......................... 198 22 549

(51) Int. Cl.$^7$ .......................... A61K 9/14; A61K 9/48; A61K 9/20
(52) U.S. Cl. .................. 424/489; 424/451; 424/464
(58) Field of Search ................ 424/489, 451, 424/464

(56) References Cited

U.S. PATENT DOCUMENTS

| | | | | | |
|---|---|---|---|---|---|
| 4,786,505 A | * | 11/1988 | Lovgren et al. | ............ | 424/468 |
| 4,865,851 A | * | 9/1989 | James et al. | ................ | 424/498 |
| 5,603,958 A | * | 2/1997 | Morein et al. | ............... | 424/489 |
| 5,948,773 A | * | 9/1999 | Akiyama et al. | | |
| 5,972,389 A | * | 10/1999 | Shell et al. | | |
| 6,328,993 B1 | * | 12/2001 | Linder et al. | ............... | 424/451 |
| 6,569,453 B2 | * | 5/2003 | Linder et al. | ............... | 424/451 |

FOREIGN PATENT DOCUMENTS

| | | | |
|---|---|---|---|
| EP | 0 005 129 | | 10/1979 |
| EP | 0 277 741 | | 8/1988 |
| EP | 0 709 087 | | 5/1996 |
| WO | WO 96/24338 | * | 8/1996 |
| WO | 97/17064 | | 5/1997 |
| WO | 98/52564 | | 11/1998 |
| WO | 99/32091 | | 7/1999 |
| WO | 00/24382 | | 5/2000 |

* cited by examiner

Primary Examiner—Thurman K. Page
Assistant Examiner—Humera N. Sheikh
(74) Attorney, Agent, or Firm—Jacobson Holman PLLC

(57) ABSTRACT

Novel administration forms for acid-labile active compounds are described. The novel administration forms have no enteric layers and are suitable for oral administration.

12 Claims, No Drawings

ADMINISTRATION FORM COMPRISING AN ACID-LABILE ACTIVE COMPOUND

This is a Divisional of application Ser. No. 09/983,990 filed Oct. 26, 2001 (now U.S. Pat. No. 6,569,453) which in turn is a continuation of Ser. No. 09/530,944 filed Jun. 22, 2000, now U.S. Pat. No. 6,328,993, which is a 371 of PCT/EP08036 filed Dec. 8, 1998.

TECHNICAL FIELD

The present invention relates to the field of pharmaceutical technology and describes a novel administration form comprising an acid-labile active compound, in particular an acid-labile proton pump inhibitor. The novel administration form is suitable for oral administration. Furthermore, the invention also relates to a process for the production of the administration form and preparations which can be used for the production of the administration form.

PRIOR ART

It is generally known to coat oral administration forms, e.g. tablets or pellets, which contain an acid-labile active compound, with an enteric coating which is rapidly dissolved in the alkaline medium of the intestine after gastric passage. An example of such acid-labile active compounds is acid-labile proton pump inhibitors ($H^+/K^+$ ATPase inhibitors), in particular pyridin-2-ylmethylsulfinyl-1H-benzimidazoles, such as are disclosed, for example, in EP-A-0 005 129, EP-A-0 166 287, EP-A-0 174 726 and EP-A-0 268 956. On account of their $H^+/K^+$ ATPase-inhibiting action, these are of great importance in the therapy of diseases which result from increased gastric acid secretion. Examples of already commercially available active compounds from this group are 5-methoxy-2-[(4-methoxy-3,5-dimethyl-2-pyridinyl)-methylsulfinyl]-1H-benzimidazole (INN: omeprazole), 5-difluoromethoxy-2-[(3,4-dimethoxy-2-pyridinyl)-methylsulfiny]-1H-benzimidazole (INN: pantoprazole), 2-[3-methyl-4-(2,2,2-trifluoroethoxy)-2-pyridinyl)-methylsulfinyl]-1H-benzimidazole (INN: lansoprazole) and 2-{[4-(3-methoxypropoxy)-3-methylpyridin-2-yl]-methylsulfinyl}-1H-benzimidazole (INN rabeprazole).

Because of their strong tendency to decompose in a neutral and, in particular, acidic environment, strongly colored decomposition products also being formed, it is also necessary in this case for oral preparations to protect the active compounds from the action of acids and moisture and destruction by undesired interaction with pharmaceutical auxiliaries. In the case of the highly acid-labile pyridin-2-ylmethylsulfinyl-1H-benzimidazoles, it is moreover necessary to process these in the tablet core or in pellets in the form of their alkaline salts, for example as sodium salts, or together with alkaline substances. Since the substances possible for enteric coatings are those having free carboxyl groups, a problem results that the enteric coating, because of the alkaline medium in the interior, begins to dissolve or is even dissolved from the inside out and the free carboxyl groups promote the decomposition of the active compounds. It is therefore necessary to provide an insulating intermediate layer (subcoating) between the enteric coating and the alkaline tablet core or pellet. In EP-A-0 244 380, it is proposed to coat cores which contain the active compound together with alkaline compounds or as an alkaline salt with at least one layer of nonacidic, inert pharmaceutically acceptable substances, which is soluble in water or rapidly disintegrates in water, before the enteric layer is applied. The intermediate layer or intermediate layers act as pH-buffering zones in which the hydrogen ions diffusing in from outside can react with the hydroxyl ions diffusing out of the alkaline core. In order to increase the buffer capacity of the intermediate layer, it is proposed to incorporate buffer substances into the intermediate layer(s). In practice, it is possible by this process to obtain preparations which are stable to a certain extent. However, relatively thick intermediate layers are needed to avoid the unattractive discolorations which occur even in the case of only slight decomposition. Additionally, a considerable effort has to be made during preparation to avoid traces of moisture.

In EP-A-0 519 365, a formulation for the active compound pantoprazole on the principle of the alkaline core coated with a water-soluble intermediate layer and an enteric layer is proposed, in which an improved stability is achieved by use of polyvinylpyrrolidone and/or hydroxypropylmethylcellulose as a binder for the alkaline core.

In EP-A-0 342 522, a formulation for acid-sensitive benzimidazoles is disclosed in which between the alkaline core and the enteric coating is situated an intermediate layer which is composed of an only slightly water-soluble film-forming material, such as ethylcellulose or polyvinyl acetate, and a slightly water-soluble fine-grain inorganic or organic material suspended therein, such as, for example, magnesium oxide, silicon oxide or sucrose fatty acid esters.

EP-A-0 277 741 describes spherical grains or granules having a core which is coated with spray powder which contains low-substituted hydroxypropyl-cellulose and a benzimidazole compound having antiulcer activity. These grains can be coated with an enteric coating agent.

WO96/01623, WO96/01624 and WO96/01625 describe an administration form for acid-labile $H^+/K^+$ ATPase inhibitors in which active compound pellets together with tablet auxiliaries are compressed to give a tablet. The pellets consist of cores which contain the acid-labile $H/K^+$ ATPase inhibitor together with alkaline compounds or as an alkaline salt. The cores of the pellets are coated with one or more layers, at least one layer having enteric properties. The enteric layer must in this case be mechanically constituted such that on compression to give tablets the acid resistance of the pellets is not adversely affected. It is mentioned that the preparation of the cores of the pellets can be effected by spray drying.

WO97/25030 describes the processing of the abovementioned pellets to give an effervescent tablet.

As the abovementioned prior art shows, the preparation of oral administration forms for acid-labile active compounds requires technically complicated processes.

DESCRIPTION OF THE INVENTION

It is an object of the present invention to provide a novel oral administration form for acid-labile active compounds in which the acid-labile active compound does not have to be protected by an enteric coating and which can be prepared without great technical effort.

It has now surprisingly been found that this object can be achieved by an administration form which comprises a plurality of individual active compound units.

The invention relates to an oral administration form comprising an acid-labile active compound and pharmaceutical auxiliaries, wherein the auxiliaries are not suitable for the formation of enteric layers (enteric coating). Preferably the active compound in the oral administration form is present in the form of a plurality of individual active compound units.

Further subjects follow from the patent claims.

The plurality of individual active compound units in the sense of the invention is a plurality of individual units (multiple individual units) in which at least one active compound particle is present. Preferably in the individual units, the active compound is surrounded by a mixture of at least one sterol and at least one polymer, by at least one fatty alcohol or by a mixture of at least one fatty alcohol and at least one polymer and/or at least one sterol.

Further subject of the invention is an oral administration form for acid-labile active compounds, comprising at least one pharmaceutical auxiliary and a plurality of individual active compound units, wherein the acid-labile active compound in the individual active compound units is surrounded by a mixture of at least one sterol and at least one polymer, by at least one fatty alcohol or by a mixture of at least one fatty alcohol and at least one polymer and/or at least one sterol.

A preferred subject of the invention is an oral administration form for acid-labile active compounds, comprising at least one pharmaceutical auxiliary and a plurality of individual active compound units, wherein the acid-labile active compound in the individual active compound units is surrounded by a mixture of at least one sterol and at least one polymer.

Further subject of the invention is an active compound unit comprising an acid-labile active compound, wherein the acid-labile active compound is surrounded by a mixture of at least one sterol and at least one polymer, by at least one fatty alcohol or by a mixture of at least one fatty alcohol and at least one polymer and/or at least one sterol.

The particle size of the individual units is advantageously less than 200 μm, preferably less than 100 μm. Preferably, the particle size is in the range from 2 μm to 50 μm, particularly preferably in the range from 4 μm to 20 μm.

Acid-labile active compounds in the sense of the present invention are, in particular, acid-labile proton pump inhibitors.

Acid-labile proton pump inhibitors ($H^+/K^+$ ATPase inhibitors) which may be mentioned in the sense of the present invention are, in particular, substituted pyridin-2-ylmethylsulfinyl-1H-benzimidazoles, such as are disclosed, for example, in EP-A-0 005 129, EP-A-0 166 287, EP-A-0 174 726, EP-A-0 184 322, EP-A-0 261 478 and EP-A-0 268 956. Preferably, mention may be made here of 5-methoxy-2-[(4-methoxy-3,5-dimethyl-2-pyridinyl)methylsulfinyl]-1H-benzimidazole (INN: omeprazole), 5-difluoromethoxy-2-[(3,4-dimethoxy-2-pyridinyl)methylsulfinyl]-1H-benzimidazole (INN: pantoprazole), 2-[3-methyl-4-(2,2,2-trifluoroethoxy)-2-pyridinyl)methyl-sulfinyl]-1H-benzimidazole (INN: lansoprazole) and 2-{[4-(3-methoxypropoxy)-3-methylpyridin-2-yl]methyl-sulfinyl}-1H-benzimidazole (INN: rabeprazole).

Further acid-labile proton pump inhibitors, for example substituted phenylmethylsulfinyl-1H-benzimidazoles, cycloheptapyridin-9-ylsulfinyl-1H-benzimidazoles or pyridin-2-ylmethylsulfinylthienoimidazoles are disclosed in DE-A-35 31 487, EP-A-0 434 999 or EP-A-0 234 485. Mention may be made by way of example of 2-[2-(N-isobutyl-N-methylamino)benzylsulfinyl]-benzimidazole (INN: leminoprazole) and 2-(4-methoxy-6,7,8,9-tetrahydro-5H-cyclohepta[b]pyridin-9-ylsulfinyl)-1H-benzimidazole (INN: nepaprazole).

The acid-labile proton pump inhibitors are chiral compounds. The term acid-labile proton pump inhibitor also includes the pure enantiomers of the acid-labile proton pump inhibitors and their mixtures in any mixing ratio including the racemates. Enantiomerically pure acid-labile proton pump inhibitors are disclosed, for example, in WO92/08716. Esomeprazole may be mentioned by way of example.

The acid-labile proton pump inhibitors are present here as such or preferably in the form of their salts with bases. Examples of salts with bases which may be mentioned are sodium, potassium, magnesium or calcium salts. If desired, the salts of the acid-labile proton pump inhibitors with bases can also be present in hydrate form. Such a hydrate of the salt of an acid-labile proton pump inhibitor with a base is disclosed, for example, in WO 91/19710.

Particularly preferred acid-labile proton pump inhibitors which may be mentioned are pantoprazole sodium and pantoprazole sodium sesquihydrate (=pantoprazole sodium× $1.5H_2O$).

The sterol is preferably a phytosterol or a zoosterol. Phytosterols which may be mentioned by way of example are ergosterol, stigmasterol, sitosterol, brassicasterol and campesterol. Zoosterols which may be mentioned by way of example are cholesterol and lanosterol. If desired, mixtures of sterols can also be present.

The polymer is preferably a polymer having nonacidic groups. Polymers which may be mentioned by way of example are polyvidone (e.g. Kollidon 17, 30 and 90 from BASF), vinylpyrrolidone/vinyl acetate copolymer and polyvinyl acetate. Cellulose ethers such as, for example, methylcellulose, ethylcellulose (Ethocel) and hydroxypropylmethylcellulose and cellulose esters (e.g. cellulose acetate phthalate) may furthermore be mentioned. If desired, mixtures of polymers can also be present.

The fatty alcohol is preferably a linear, saturated or unsaturated primary alcohol having 10–30 carbon atoms. Fatty alcohols which may be mentioned by way of example are cetyl alcohol, myristyl alcohol or stearyl alcohol. If desired, mixtures of fatty alcohols can also be present.

The amount (in % by weight) of active compound in the individual active compound unit is advantageously 1–90%. In case of units in which at least one active compound particle is present, surrounded by a mixture of at least one sterol and at least one polymer the amounts of sterol and of polymer are in each case advantageously 5–80%. Preferably, the amount of active compound is 10–50%, the amount of sterol is 10–40% and the amount of polymer is 10–50%.

In case of units in which at least one active compound particle is present, surrounded by at least one fatty alcohol, preferably the amount of active compound is 2–70% and the amount of fatty alcohol is 30–98%.

In case of units in which at least one active compound particle is present, surrounded by at least one fatty alcohol and at least one sterol, preferably the amount of active compound is 2–70%, the amount of fatty alcohol is 20–90% and the amount of sterol is 8–50%.

In case of units in which at least one active compound particle is present, surrounded by at least one fatty alcohol and at least one polymer, preferably the amount of active compound is 10–60%, the amount of fatty alcohol is 10–50% and the amount of polymer is 10–40%.

In case of units in which at least one active compound particle is present, surrounded by at least one fatty alcohol, at least one polymer and at least one sterol, preferably the amount of active ingredient is 2–70%, the amount of fatty alcohol is 20–85%, the amount of polymer is 2–25% and the amount of sterol is 10–50%.

It is possible for the person skilled in the art, on account of his/her expert knowledge, to select the best suited sterols and polymers depending on the active compound.

The individual active compound units can be prepared, for example, by spray-congealing (spray solidification) or preferably by spray-drying. Preferably spray-drying is used for the preparation of individual active compound units in which the active compound is surrounded by a mixture of at least one sterol and at least one polymer. Spray-drying takes place from a suitable solvent. Suitable solvents for the spray drying are preferably those in which the sterol and the polymer are soluble, while the active compound is insoluble. Suitable solvents can also be solvent mixtures.

If an acid-labile proton pump inhibitor, in particular a substituted pyridin-2-ylmethylsulfinyl-1H-benzimidazole, is employed as an active compound, the suitable solvents are, for example, hydrocarbons, chlorinated hydrocarbons and ethyl acetate. Hydrocarbons which may be mentioned are, in particular, linear or branched alkanes or alternatively cycloalkanes. Examples of linear alkanes are pentane, hexane and heptane. Examples of branched alkanes which may be mentioned are 2-methylpentane and 3-methylpentane. Examples of cycloalkanes which may be mentioned are cyclohexane and cyclopentane. If desired, mixtures of the hydrocarbons such as, for example, petroleum ether can also be employed. As a chlorinated hydrocarbon, chloroform and preferably dichloromethane may be mentioned.

On account of his/her expert knowledge in the field of spray drying and, if necessary, by means of customary tests, it is possible for the person skilled in the art, depending on the active compound employed, to select the best suited sterols, polymers and solvents.

For spray-drying, the sterol and the polymer are dissolved in the suitable solvent and the active compound is suspended therein. If desired, the active compound can also be suspended first and the sterol and polymer then dissolved. The suspension obtained is then sprayed in a spray drier.

Spray drying is carried out in a manner known per se. A detailed presentation of this technique is found in K. Masters, Spray Drying Handbook, 5th edition 1991, and J. Broadhead, S. K. Edmond Ronan, C. T. Rhodes. The Spray Drying of Pharmaceuticals, Drug Dev. Ind. Pharm. 18, 1169 (1992). The principle of spray drying consists in breaking down a solution or suspension of the product to be dried into fine droplets and drying it using a hot stream of gas. The solid components remaining after evaporation of the solvent are separated off from the stream of gas by means of a cyclone and/or by a filter unit and collected.

Possible drying gases are, in particular, air and preferably nitrogen. The gas inlet temperature depends on the solvent.

Further subject of the invention is a preparation comprising an acid-labile active compound, at least one sterol and at least one polymer obtainable by spray-drying of a suspension of the acid-labile active compound in a solution of the sterol and the polymer in a suitable solvent.

Preferably spray-congealing is used for the preparation of individual active compound units in which the active compound is surrounded by at least one fatty alcohol or by a mixture of at least one fatty alcohol and at least one polymer and/or at least one sterol.

For spray-congealing the fatty alcohol is fused and, if desired, the polymer and/or the sterol are dissolved therein to give a homogeneous solution. The active compound is then suspended in the solution. The suspension obtained is then sprayed in a spray-dryer.

Spray-congealing is carried out in a manner known per se. A detailed presentation of this technique is found for example in P. B. Deasy, Microencapsulation and Related Drug Process (1984).

Further subject of the invention is a preparation comprising an acid-labile active compound, at least one fatty alcohol or a mixture of at least one fatty alcohol and at least one polymer and/or sterol obtainable by spray-congealing of a suspension of the acid-labile compound in a solution, if desired, of the polymer and/or sterol in the fatty alcohol.

The particle size of the active compound used in the spray-drying or spray-congealing process is advantageously less than 100 μm, preferably less than 40 μm. Preferably, the particle size is in the range from 1–20 μm, particularly preferably in the range from 3–15 μm. Such particle size of the active compound for example can be achieved by milling the active compound in a suitable mill.

The individual active compound units, subsequently also designated as preparations, can then serve as a base for the production of the oral administration forms according to the invention. Examples of oral administration forms according to the invention to which the preparations can be processed are solutions, suspensions, emulsions, gels, tablets, effervescent tablets, powder in sachets, coated tablets or capsules. The person skilled in the art is familiar on the basis of his/her expert knowledge with auxiliaries which are suitable for the desired administration form. For the administration forms, it is surprisingly possible to dispense with the enteric coating and in spite of this to achieve a therapeutic action on oral administration.

The oral administration forms according to the invention contain the acid-labile active compound in a dose customary for the treatment of the appropriate disorder. The oral administration forms according to the invention comprising acid-labile proton pump inhibitors are suitable for the treatment and prevention of all diseases for the treatment or prevention of which pyridin-2-ylmethylsulfinyl-1H-benzimidazoles are employed. In particular the oral administration forms according to the invention can be employed in the treatment of diseases of the stomach. Thus, the oral administration forms according to the invention contain between 1 and 500 mg, preferably between 5 and 60 mg, of an acid-labile proton pump inhibitor. Examples which may be mentioned are tablets or capsules which contain 10, 20, 40 or 50 mg of pantoprazole sodium sesquihydrate. The daily dose (e.g. 40 mg of active compound) can in this case be administered in the form of a single administration or in several administrations using the oral administration forms according to the invention.

The oral administration forms comprising acid labile compounds according to the invention can also be combined with other active compounds, either in fixed or in free combination. Fixed combination in this connection relates to an administration form wherein all active compounds are present in a single dosage unit. Free combination in this connection relates to an administration form, wherein the active compounds are present in separated dosage units. In connection with oral administration forms comprising acid-labile proton pump inhibitors a combination with antimicrobially active compounds or NSAIDs (non steroidal anti inflammatory drugs) may be mentioned. Particularly mention may be made of a combination with antimicrobially active compounds which can be used in the control of *Helicobacter pylori* (*H. pylori*).

Examples of suitable antimicrobially-active ingredients (active against *Helicobacter pylori*) are enumerated in European Patent Application EP-A-282131. These active ingredients include, for example, bismuth salts (such as bismuth subcitrate or bismuth subsalicylate), sulfonamides, nitrofurans (such as nitrofurazone, nitrofurantoin or furazolidone), metronidazole, tinidazole, nimorazole or antibiotics. Examples of antibiotics which may be mentioned in this connection are, arranged according to particular classes of active ingredient: aminoglycosides, such as gentamicin, neomycin, kanamycin, amikacin or streptomycin; macrolides, such as erythromycin, azithromycin, clarithromycin, clindamycin or rifampicin; penicillins, such as penicillin G, penicillin V, ampicillin, mezlocillin or amoxicillin; polypeptides, such as bacitracin or polymyxin; tetracyclines, such as tetracycline, chlorotetracycline, oxytetracycline, minocycline or doxycycline; carbapenems, such as imipenem, loracarbef, meropenem or panipenem; cephalosporins, such as cefalexin, cefoxitin, cefuroxime axetil, cefotaxime, cefpodoxime proxetil, cefaclor, cefadroxil or cephalothin; gyrase inhibitors, such as ciprofloxacin, norfloxacin, ofloxacin or pefloxacin; or other different antibiotics, such as chloramphenicol. Particularly worthy of mention in this connection is also the combination of a plurality of antimicrobially-active ingredients, for example the combination of a bismuth salt and/or tetracycline with metronidazole, or the combination of amoxicillin or clarithromycin with metronidazole and amoxicillin with clarithromycin.

Particularly worthy of mention in this connection is also administration of a proton pump inhibitor together with a plurality of antimicrobially-active ingredients, for example with the combination of a bismuth salt and/or tetracycline with metronidazole or with the combination of amoxicillin or clarithromycin or with metronidazole.

The preparation of administration forms according to the invention is described by way of example below. The example below illustrate the invention in greater detail without restricting it.

Production of the Preparations by Spray-Drying

EXAMPLE 1

7.0 g of cholesterol and 5.0 g of Ethocel are dissolved in 100 ml of dichloromethane. 5.0 g of pantoprazole sodium sesquihydrate are suspended in the solution. The suspension is spray-dried in a laboratory spray-dryer (Büchi Mini Spray Dryer B191). Spray conditions: drying gas nitrogen, inlet temperature 51° C.; pump output 10%. A white, free-flowing powder is obtained.

EXAMPLE 2

5.0 g of cholesterol and 5.0 g of Kollidon 17 are dissolved in 80 ml of dichloromethane. 5.0 g of omeprazole magnesium are suspended in the solution. The suspension is spray-dried in a laboratory spray-dryer (Büchi Mini Spray Dryer B191). Spray conditions: drying gas nitrogen, inlet temperature 51° C.; pump output 10%. A white, free-flowing powder is obtained.

EXAMPLE 3

5.0 g of cholesterol and 8.0 g of polyvidone 17 PF are dissolved in 60 ml of dichloromethane. 5.0 g of pantoprazole sodium sesquihydrate are suspended in the solution. The suspension is spray-dried in a laboratory spray-dryer (Büchi Mini Spray Dryer B191). Spray conditions: drying gas nitrogen, inlet temperature 52° C.; pump output 12%. A white, free-flowing powder is obtained.

EXAMPLE 4

5.0 g of cholesterol and 8:0 g of polyvidone 17 PF and 2.0 g of ethylcellulose are dissolved in 60 ml of dichloromethane. 5.0 g of pantoprazole sodium sesquihydrate are suspended in the solution. The suspension is spray-dried in a laboratory spray-dryer (Büchi Mini Spray Dryer B191). Spray conditions: drying gas nitrogen, inlet temperature 52° C.; pump output 12%. A white, free-flowing powder is obtained.

EXAMPLE 5

5.0 g of β-sitosterol, 8.0 g of polyvidone 17 PF and 1.0 g of ethylcellulose are dissolved in 60 ml of dichloromethane. 5.0 g of pantoprazole sodium sesquihydrate are suspended in the solution. The suspension is spray-dried in a laboratory spray-dryer (Büchi Mini Spray Dryer B191). Spray conditions: drying gas nitrogen, inlet temperature 52° C.; pump output 12%. A white, free-flowing powder is obtained.

The preparations obtained according to Examples 1 to 5 have a particle size in the range 10–40 $\mu$m. By variation of the spraying conditions, it is possible, for example, to obtain larger or smaller particles.

Production of the Preparations by spray-Congealing

EXAMPLE 6

100 g of cetyl alcohol are heated to 65° C. 50 g of pantoprazole sodium sesquihydrate are slowly added. The mixture is stirred until a homogeneous suspension is obtained and subsequently sprayed through a nozzle in a spray dryer.

EXAMPLE 7

80 g of stearyl alcohol and 10 g of ethylcellulose are heated to 70° C. and stirred until a clear solution is obtained. 40 g of pantoprazole sodium sesquihydrate are added and stirred. The homogeneous suspension is spray-congealed in a spray dryer.

Preparation of the Administration Forms

EXAMPLE A

Granules 134.7 g of mannitol, 30 g of Kollidon 30 and 20 g of xanthan are mixed dry. The mixture is granulated with water in a fluidized bed granulator. Granules having a particle size of 0.8–1.5 mm are obtained, which are mixed with the preparation (15.3 g) obtained according to Example 1. The mixture thus obtained is filled into sachets or compressed to give tablets—if desired together with further tablet auxiliaries—in a manner known to the person skilled in the art.

EXAMPLE B

An amount corresponding to 22.6 mg pantoprazole sodium sesquihydrate of the powder formulation as described in Example 5 is mixed with appropriate amounts of lactose. This mixture is flavoured according to individual taste and filled into minibags (Sachets) each containing one individual dose. The contents of one minibag are dispersed in a glass of tap water under stirring to obtain a suspension for oral intake.

EXAMPLE C

An amount corresponding to 45.2 mg pantoprazole sodium sesquihydrate of the powder formulation as described in Example 1 is mixed with appropriate amounts of lactose. This mixture is combined with a mixture of citric acid and sodium carbonate. After addition of a suitable lubricant (e.g. sodium stearyl fumarate) and appropriate flavouring the mixture is directly (without further granulation) compressed to effervescent tablets. One tablet is to be thrown into a glass of water to obtain a drinking suspension after tablet disintegration.

EXAMPLE D

An amount corresponding to 45.2 mg pantoprazole sodium sesquihydrate of the powder formulation as described in Example 4 is mixed with appropriate amounts of (fast flowing) lactose for improvement of powder flow properties. This mixture is filled into appropriately sized hard gelatine capsules together with suitable concomitant medication like antibiotics (e.g. amoxicillin for *Helicobacter pylori* eradication) or NSAIDs (non steroidal anti inflammatory drugs) in available dosage forms.

What is claimed is:

1. A method of orally administering an effective amount of a stable form of acid-labile active compound to a subject in need of such therapy, wherein the active compound is in an enteric-coating-free oral administration form comprising a pharmaceutical auxiliary and a plurality of individual compound units, wherein the acid-labile active compound in the individual active compound units is a) a proton pump inhibitor, b) a salt of a proton pump inhibitor with a base or c) a hydrate of (b), surrounded by a mixture of at least one sterol and at least one polymer.

2. A method of orally administering an effective amount of a stable form of acid-labile active compound to a subject in need of such therapy, wherein the active compound is in an enteric-coating-free oral administration form comprising a pharmaceutical auxiliary and a plurality of individual compound units, wherein the acid-labile active compound in the individual active compound units is a) a proton pump inhibitor, b) a salt of a proton pump inhibitor with a base or c) a hydrate of (b), surrounded by at least one fatty alcohol.

3. A method of orally administering an effective amount of a stable form of acid-labile active compound to a subject in need of such therapy, wherein the active compound is a) a proton pump inhibitor, b) a salt of a proton pump inhibitor with a base or c) a hydrate of (b), in an enteric-coating-free oral administration form comprising a pharmaceutical auxiliary and a plurality of individual compound units, wherein the acid-labile active compound in the individual active compound units is surrounded by a mixture of at least one fatty alcohol and at least one polymer.

4. A method of orally administering an effective amount of a stable form of acid-labile active compound to a subject in need of such therapy, wherein the active compound is a) a proton pump inhibitor, b) a salt of a proton pump inhibitor with a base or c) a hydrate of (b), in an enteric-coating free oral administration form comprising a pharmaceutical auxiliary and a plurality of individual compound units, wherein the acid-labile active compound in the individual active compound units is surrounded by a mixture of at least one fatty alcohol and at least one sterol.

5. A method of orally administering an effective amount of a stable form of acid-labile active compound to a subject in need of such therapy, wherein the active compound is a) a proton pump inhibitor, b) a salt of a proton pump inhibitor with a base or c) a hydrate of (b), in an enteric-coating-free oral administration form comprising a pharmaceutical auxiliary and a plurality of individual compound units, wherein the acid-labile active compound in the individual active compound units is surrounded by a mixture of at least one fatty alcohol, at least one polymer and at least one sterol.

6. A method of orally administering an effective amount of a stable form of acid-labile active compound to a subject in need of such therapy, wherein the active compound is in an enteric-coating-free oral administration form comprising a pharmaceutical auxiliary and a plurality of individual compound units, wherein the acid-labile active compound in the individual active compound units is surrounded by a) at least one fatty alcohol, b) a mixture of at least one sterol and at least one polymer, or c) a mixture of at least one fatty alcohol and at least one polymer and/or at least one sterol, and wherein the acid-labile active compound is an acid labile proton pump inhibitor, a salt of an acid-labile proton pump inhibitor with a base, and a hydrate of a salt of an acid-labile proton pump inhibitor with a base.

7. A method of claim 6, wherein the acid-labile active compound is pantoprazole, omeprazole, esomeprazole, lansoprazole or rabeprazole.

8. A method of claim 6 wherein the acid-labile active compound is in combination with a non-steroidal anti-inflammatory drug (NSAID).

9. A method of claim 6 which comprises separately administering an NSAID to the subject.

10. A method of claim 6 wherein the acid-labile active compound is in combination with an antimicrobially active compound.

11. A method of claim 6 which comprises separately administering an antimicrobially active compound to the subject.

12. A method of claim 6 which further comprises administering to the subject an antimicrobially active compound of a type and in an amount suitable to control *Helicobacter pylori*.

* * * * *